US006970760B2

(12) United States Patent
Wolf et al.

(10) Patent No.: US 6,970,760 B2
(45) Date of Patent: Nov. 29, 2005

(54) PRODUCTION OF REPLACEMENT TEETH FROM A THREE-DIMENSIONALLY DETERMINED AND DIGITIZED POSITIVE MODEL

(75) Inventors: Dietrich Wolf, Hanau (DE); Stefan Fecher, Johannesberg (DE); Andrea Pest, Mainaschaff (DE); Lothar Völkl, Goldbach (DE)

(73) Assignee: DeguDent GmbH, Hanau (DE)

( * ) Notice: Subject to any disclaimer, the term of this patent is extended or adjusted under 35 U.S.C. 154(b) by 11 days.

(21) Appl. No.: 10/480,798

(22) PCT Filed: Jul. 2, 2002

(86) PCT No.: PCT/EP02/07282

§ 371 (c)(1),
(2), (4) Date: Dec. 19, 2003

(87) PCT Pub. No.: WO03/007834

PCT Pub. Date: Jan. 30, 2003

(65) Prior Publication Data

US 2004/0158342 A1    Aug. 12, 2004

(30) Foreign Application Priority Data

| Jul. 13, 2001 | (DE) | ................. 101 33 569 |
| Sep. 13, 2001 | (DE) | ................. 101 45 104 |
| Nov. 2, 2001 | (DE) | ................. 101 53 649 |

(51) Int. Cl.$^7$ .......................... A61C 13/00; G06F 19/00
(52) U.S. Cl. ...................... 700/163; 700/118; 700/159; 433/213; 433/223
(58) Field of Search ....................... 700/118, 159, 163; 433/173, 213, 223

(56) References Cited

U.S. PATENT DOCUMENTS

| 4,478,580 | A | * | 10/1984 | Barrut ........................ 433/223 |
| 5,452,219 | A | * | 9/1995 | Dehoff et al. ............... 700/163 |
| 5,857,853 | A | * | 1/1999 | van Nifterick et al. ..... 433/213 |
| 6,558,162 | B1 | * | 5/2003 | Porter et al. ................. 433/173 |
| 6,790,040 | B2 | * | 9/2004 | Amber et al. ................ 433/173 |

FOREIGN PATENT DOCUMENTS

| DE | 19642247 | 1/1998 |
| EP | 0774933 | 12/2000 |
| WO | 9427523 | 12/1994 |
| WO | 9947065 | 9/1999 |

OTHER PUBLICATIONS

Haas et al, "Der Randspalt von Metall-und Nichtmetallgetragenen Keramikkronen im Vergleich", Die Quintessenz, Apr., 1998, pp. 625-633.

* cited by examiner

Primary Examiner—Jayprakash N. Gandhi
(74) Attorney, Agent, or Firm—Dennison, Schultz, Dougherty & MacDonald

(57) ABSTRACT

A method for the production of replacement teeth (5) from a three-dimensionally determined and digitized model, whereby for improved handling, cost and quality of the produced replacement tooth (5) a method including the following steps is carried out: inputting the data for the digitized model, treating the inner surface (9) of the surface model with a given offset value to generate a cement gap (7, 8) between the tooth replacement (5) to be made and tooth stump (1, 2) and calculation of a program for machining the blank or a mold by means of a machine tool.

24 Claims, 2 Drawing Sheets

PRODUCTION OF REPLACEMENT TEETH FROM A THREE-DIMENSIONALLY DETERMINED AND DIGITIZED POSITIVE MODEL

BACKGROUND OF THE INVENTION

The invention relates to a method for the production of a dental prosthesis to be fastened to a tooth stump consisting of a three-dimensionally mapped and digitized positive model which comprises the following steps:
  inputting the data of the digitized positive model;
  machining the inner surface of the positive model with a preset offset value to form a gap between a future dental prosthesis and the tooth stump, and
  calculating a program for machining a blank by means of a machine tool to produce the dental prosthesis.

In particular, the invention relates to the field of producing basic structures for dental prostheses, in particular for dental crowns and/or bridges for fastening to prepared natural and/or artificial tooth stumps or the like.

A number of devices and methods for producing artificial dental bridges and crowns are known. Generally, after the dental preparation in which the teeth used for anchoring are prepared by grinding for receiving a crown or bridge or for which, e.g. a pin is implanted, an impression of the tooth stump, the surrounding area and jaw is made. This is usually done with silicone sealing compounds, but other materials are also known.

A so-called master model can be made from the impression by means of a plaster cast. This master model shows the situation in the patient's mouth positively. In this model, the dental technician with his handicraft skills fashions a model of the basic structure of the dental prosthesis from wax or from plastic which melts at a low temperature or hardens in a polymerizing manner (positive model). In this case, the dental technician can also take the counter occlusion of the other jaw into account by means of the master model in hand.

Traditionally, the model produced by the dental technician is embedded and melted in heat-resistant substances. The basic structure can be made by precision casting in conventional metal dental alloys in the mold thus produced.

For cosmetic reasons, a facing in ceramic or plastic is usually also made, at least in the area of the front teeth.

It is known from WO 99/47065 to completely digitalize the outer and inner surface of the structural model after a wax model has been formed. A model which inadequately reflects the situation in the patient's mouth is then mathematically completed with respect to the three-dimensional outer and inner surface. The result of the digitalization and a mathematical completion should represent a digital description of the complete surface of the basic structure of the prosthesis.

In order to be able to machine a blank consisting of porous ceramics with the data obtained from the digitalization of the wax model, it is described in detail in WO 99/47065 that the dimensions of the surface model of the digitized body are linearly enlarged in all spatial directions to compensate for the shrinkage of the blank during sintering. The enlargement factor f should thereby result from a specific function according to the ratio of the density of the blank and a basic bridge structure produced therefrom.

The control commands for a processing machine are to be generated from the data of the enlarged surface with which the enlarged basic bridge structure is to be carved out of the blank. In comparison to the mathematically enlarged surface of the basic bridge structure, no offset is provided, whereby the machined surface is to obtain exactly the same measurements vis-á-vis the digitized body after the sintering shrinkage. Furthermore, no subsequent processing should take place.

In addition, it is proposed in WO 99/47065 to use a blank for the production of the basic bridge structure in which a machine or visually readable identification code containing the enlargement factor f is affixed to the blank itself or to its packaging, to a tag or an enclosed packaging slip.

The wax model of the basic bridge structure should be produced positively on a plastic impression of the negative form of the prepared tooth stump produced from a silicone mass, whereby the tooth stumps should first be coated by hand with a spacer coating composition to later form a cement gap.

The digitalization is accomplished mechanically or optically. For this purpose, reference is made to methods for the digitalization in the mouth of a patient on a prepared tooth stump or to a model, said methods being known, for example, from U.S. Pat. No. 4,182,312 with respect to a mechanical digitalization and from EP 0 054 785 A1 with respect to an optical digitalization.

The fundamental disadvantage of the mechanical digitalization known from U.S. Pat. No. 4,182,312 is in the fixing of the mechanical scanning device to the patient since the scanning is to take place directly in the oral cavity of the patient. The secure handling of the device in the narrow oral cavity is equally problematic. A processing machine for producing dental prostheses should be controlled directly with the scanning of teeth and surrounding tissue as in a duplicating milling machine.

To this end, a probe having a transmission rod securely fixed to it must be moved by the dentist over the surfaces in the patient's mouth that are of interest. A complete detection of the surface requires very many scanning movements, which is very stressful for the patient due to the time required. Furthermore, the probe tips must be changed depending on the shape of the processing tool.

With the method described in EP 0 054 785 A1, an image recording head is to be inserted into a patient's mouth. This image recording head is to detect a three-dimensional image of a tooth cavity or the like. For this purpose, the image data is to be shown on a computer screen, so that a dentist can check to see whether the positioning of the image recording head enables a sufficiently accurate image. If necessary, the image recording head can be changed accordingly to a more favorable position.

When a proper position has been obtained, a three-dimensional image of the tooth cavity or the like should be formed spatially true to size—without further explanation. The appropriate data is then to be completed by interpolation and manual processing of the data set in the manner of a CAD construction, until a corresponding dental prosthesis body has been completely formed. The corresponding data should then be used to make a suitable blank in order to produce a suitable dental prosthesis directly from the image while avoiding the aforementioned skilled production steps.

The awkward manipulation with the camera in the patient's mouth was also found to be disadvantageous in practice with this method, in particular, it requires great discipline on the part of the patient.

Furthermore, as described in the aforementioned document, it is necessary to coat the tooth to be mapped with a powder to obtain defined reflection conditions, since the natural dental material has translucent properties. Due to the translucent properties, light could otherwise penetrate partially uncontrolled into the tooth stump to be measured and perhaps be reflected in deeper layers which would result in an inaccurate result. However, the coating with a reflection powder simultaneously increases the inaccuracy by the application of the powder which will inherently and, based on the restricted conditions in the patient's mouth, always be irregular in practice. The limited resolving power of the image recorder and the difficult lighting conditions in the mouth to be mapped are also disadvantageous.

A method for producing dental prosthesis parts is known from DE 196 42 247 C1 according to which a prepared tooth is digitized in order to then produce a dental prosthesis taking the digitized model teeth into consideration. To produce a dental prosthesis, according to WO 94/27523, a tooth is measured, a part of a tooth is prepared, a tooth impression or a copy of the tooth is made. The triangulation method is used for the measuring.

A powder-metallurgical production process for an accurately shaped dental prosthesis is known from EP 0 774 933 B1. In this case, the three-dimensional optical or mechanical inputting of the prepared tooth takes place directly in the mouth or on a plaster model. The cement layer, by means of which the dental prosthesis is joined with the prepared tooth, is also taken into consideration when producing the dental prosthesis.

Independent of the type of production of the dental prosthesis, for aesthetic reasons, care is taken to make it as slender as possible. From experience, the dental model is also formed primarily from an aesthetic point of view to have sufficient space for the subsequent facing. As a result, the necessity for a sufficient mechanical construction is disregarded and the life of the dental prosthesis produced in accordance with it is adversely affected.

SUMMARY OF THE INVENTION

The object of the present invention is to further develop a method for the production of dental prostheses of the aforementioned type in such a way that the dental prosthesis of this type has sufficient strength to achieve a long service life, it being simultaneously ensured that the dental prosthesis has a sufficient aesthetic effect and corresponds to the appearance of a natural tooth. An improved method with respect to handling, cost efficiency and quality of the dental prosthesis thus produced is also to be provided.

According to the invention, the object is essentially solved in that as material for the dental prosthesis one is employed which has, in normal use of the dental prosthesis, a maximum tensile stress occurring which corresponds to about 0.1–0.7 times the tensile strength of the material employed.

In particular, the maximum tensile stress in the dental prosthesis should correspond to $\leq 0.5$ times, in particular 0.2–0.5 times, the tensile strength of the material used.

By means of the teaching according to the invention, the dental prosthesis is designed in its dimensioning with respect to the loading due to tensile stresses, whether it be, for example, in the wall thickness, whether it be for example in the material cross-section or the connection radii in bridge elements in the area between supports formed by tooth stumps. As a result, it is ensured that the dental prosthesis has the required strength without having to accept the loss of its aesthetical appearance. In other words, a slender appearance can still be given without the risk of failure occurring under normal stress of the dental prosthesis. In its dimensioning, the dental prosthesis is thereby directed, with respect to the especially strongly stressed areas, to the strength of the material used. For example, if $Al_2O_3$ is used as ceramic material for a dental prosthesis, then the tensile strength of the material is 350 $N/mm^2$, so that a maximum tensile stress between 35 and 245 $N/mm^2$, in particular about 175 $N/mm^2$, may occur in the area which is most stronly loaded. In bridges, this maximum tensile stress occurs in the transitional area between the bridge elements and the posts formed by the tooth stumps. If $Y_2O_3$—stabilized $ZrO_2$, which has a strength of 650 $N/mm^2$, is used as ceramic material, then the dimensions of the dental prosthesis must be designed accordingly such that a maximum tensile stress of between 65 and 455 $N/mm^2$, in particular $\leq 325$ $N/mm^2$, occurs in the most strongly area.

Furthermore, the offset value should be preset dependent on the axis.

Furthermore, by means of the teaching according to the invention, a reliable and precise gap for receiving cement or other binding agents for securing the dental prosthesis on the prepared tooth stump can be obtained with the desired extent of the clearances. In this way, the risk of the known methods resulting from the manual application of spacer coating compositions with respect to maintaining the optimal thickness, uniformity and reproducibility of the application can be excluded. In particular, due to the axis-dependent formation of the gap, it is ensured that an optimal fit of the dental prosthesis on the tooth stump and their interconnection is made possible.

It is advantageous for all current fastening techniques for a crown or a bridge on a tooth stump if the offset value is up to 150 $\mu$m.

The smallest gap dimensions in the area of the contact surface of a dental prosthesis and tooth stump, and thus an especially good resistance to a future caries attack, can be obtained if the gap differs from a low value at the periphery of the cavity defined by the inner surface of the positive model to a larger value in the tip of the cavity, in particular, if the gap on the periphery of the cavity is less than 5 $\mu$m, preferably less than 2.8 $\mu$m, especially preferred not more than 1.5 $\mu$m.

The method of the invention is also especially secure without operator intervention if it is further characterized by the following step: conducting a plausibility test of the data with reference to the data of adjacent areas of the positive model and, optionally, issuance of a warning.

In a further advantageous embodiment, the method is further characterized by the following step: replacement, preferably of individual missing data points or of non-plausible data points by interpolated values with reference to the data of adjacent areas of the positive model and smoothing the outer and/or inner surface of the data of the positive model by means of a smoothing function.

To prevent a formation of hollow spaces between dental prosthesis and tooth stump, from which a further caries attack of the tooth stump and thus a destruction of the support tooth of a bridge can usually be expected, the method is advantageously further characterized by the following step: conducting a test of the data of the inner surface of the positive model for undercuts with reference to the data of adjacent areas of the positive model and, optionally, issuance of a warning.

For an especially high security against breakage of the dental prosthesis during later use by the patient, the method is further characterized by the following step: calculating the wall thickness of the positive model by comparing the data of the inner surface of the positive model with the data of the outer surface of the positive model and comparing the value of the wall thickness with a wall thickness minimum value, correcting the data of the outer side of the positive model such that at least the wall thickness minimum value is maintained and/or a warning issued, in particular if the minimum value of the wall thickness is at least about 0.5 mm, preferably about 0.1 mm, in particular at least about 0.3 mm.

To ensure a favourable shaping of the dental prosthesis, it is also advantageous if it is ensured by comparison of the radii of the outer and/or inner surfaces of the positive model with a minium radius of at least about 0.1 mm, preferably about 0.2 mm, in particular 0.3 mm, and correction of the data of the outer and/or inner surface of the positive model, that at least the minimum radius is obtained and/or a warning issued.

To produce an especially stable and durable bridge, the method is further characterized by the following step: calculation of the material cross-section in bridge elements in the area between two posts formed by tooth stumps, comparison of the cross-section with a minimum value, correction of the data of the outer side of the positive model such that at least the minimum value is maintained and/or issuance of a warning, in particular if the minimum value is at least about 2 $mm^2$, preferably about 5 $mm^2$, in particular at least about 7 $mm^2$.

To prevent a too narrow cavity of the dental prosthesis when preparing the top of the tooth stump which does not have a sufficient roundness for conventional milling cutters, the method is further characterized by the following step: calculation of the radii of the inner surface of the positive model, comparison of the values of the radii with a minimum radius, correction of the data of the inner surface of the positive model such that the cavity is enlarged to such an extent that at least the minimum radius is obtained and/or a warning issued.

Depending on how the machine tool to be used is controlled, it can be expedient if the method is further characterized by the following step: machining of the positive model with a preset offset value to adapt it to the tool contour during subsequent processing.

To produce dental prostheses from blanks which are subject to a change in dimensions after the mechanical processing during production, e.g. ceramic blanks that are not sintered or presintered, which must then be completely sintered after the shaping work and thereby shrink, the method according to the invention is especially advantageously further characterized by the following step: processing the data of the positive model with an enlargement factor to compensate for shrinkage or swelling of the material for a dental prosthesis during production, in particular for a good fit when the enlargement factor is non-linear and/or anisotropic.

An especially accurately fitting dental prosthesis can be obtained, in particular with really anisotropic or inhomogeneous blanks, if the enlargement factor is determined by a three-dimensional transfer function $f(x, y, z)$, the three-dimensionally transfer function $f(x, y, z)$ expediently being determined by the three-dimensional density distribution $F(x, y, z)$ of the ceramic blank.

For the largely automatic production, the method is advantageously further characterized by reading the transfer function $f(x, y, z)$ or density distribution $F(x, y, z)$ allocated to a blank to be processed from a data carrier, in particular if the data carrier is a bar code label, a transponder label which can be read out via a inputting device or a data bank which can be accessed via identification means attached to or with the blank.

Further details, advantages and features of the invention can be found not only in the claims, in the features to be found therein—separately and/or in combination—but also in the following description of the preferred embodiments found in the drawing, in which:

DETAILED DESCRIPTION OF THE INVENTION

Figure 1:
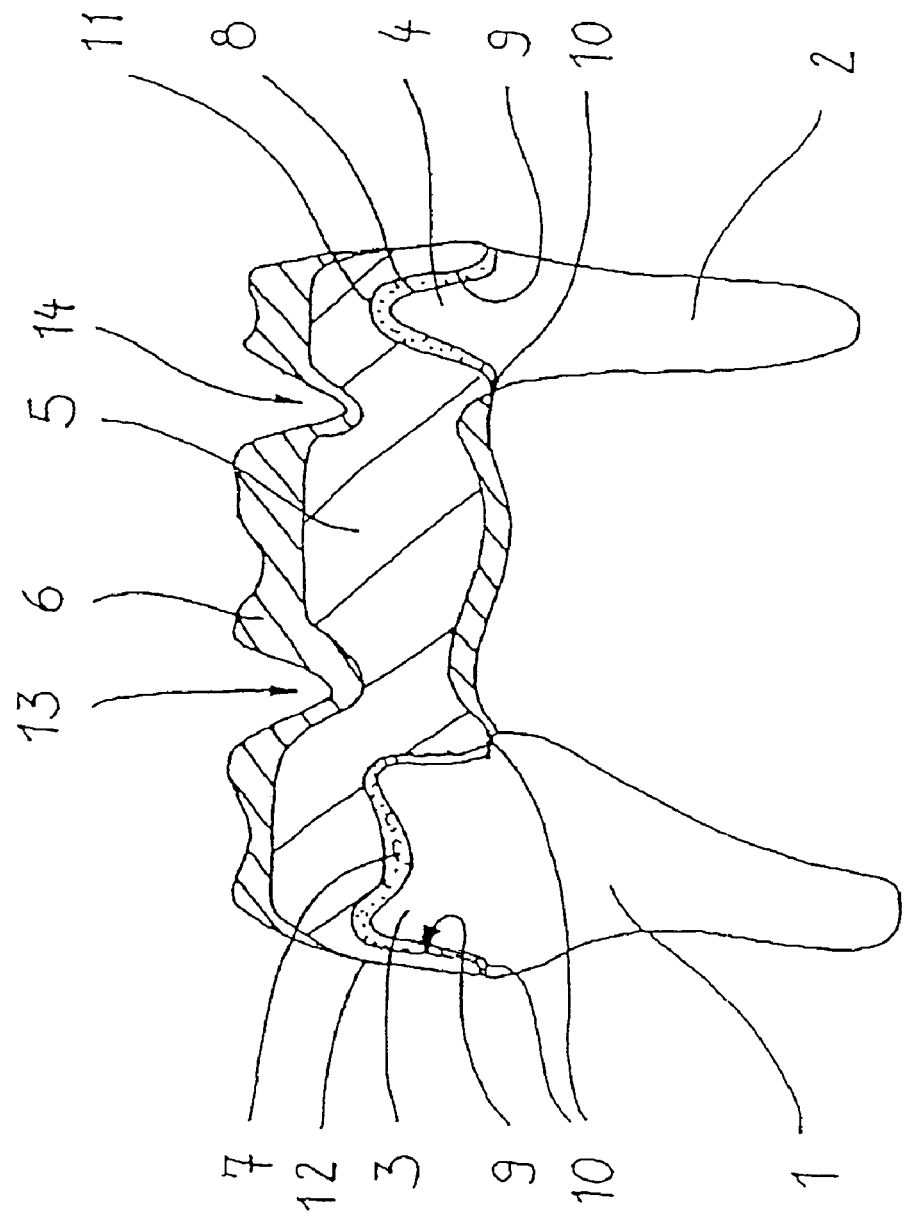
FIG. 1 shows a schematic crosssection through two tooth stumps with a dental prosthesis in the form of a bridge.
Figure 2:
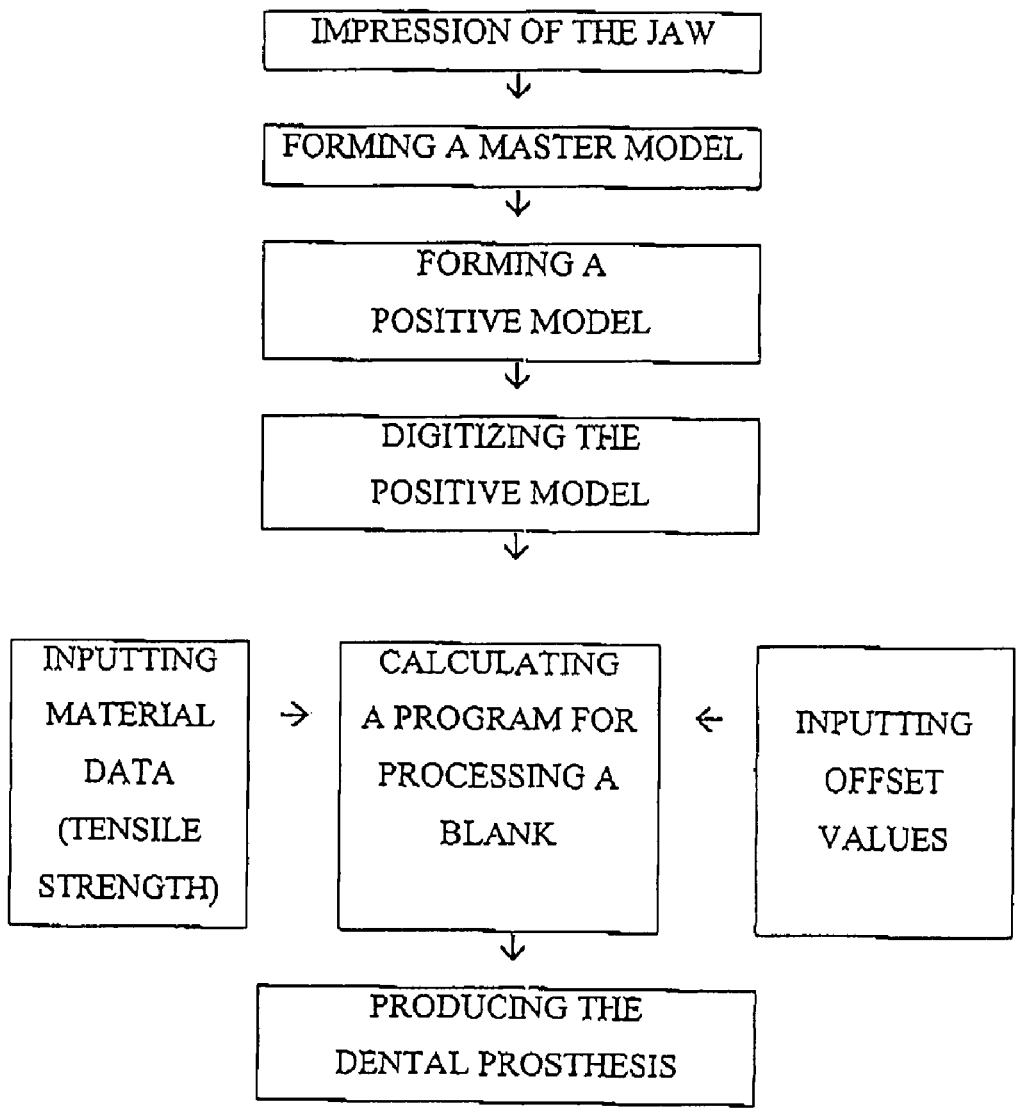
FIG. 2 is a flow chart showing the method steps for producing a dental prosthesis in accordance with the claimed invention.

FIG. 1 shows two prepared tooth stumps 1 and 2 which are to be smoothed in their upper areas 3 and 4 for receiving a dental prosthesis. In this case, the dental prosthesis comprises a basic bridge structure 5 which is, in addition, provided with a facing 6 in a conventional manner for producing the visual and masticatory surfaces. The basic bridge structure 5 is fastened in each case to the tooth stumps 1, 2 by means of a layer of a dental cement in the cement gaps 7 and 8.

For reasons of clarity, in particular the gap 7, 8 such as cement gaps are illustrated completely untrue to scale.

To produce the dental prosthesis, i.e. in the embodiment, the basic bridge structure 5 with the facing 6 with the desired gaps 7, 8, a master model of the jaw in which the dental prosthesis is to be placed is firstly produced according to the invention. The master model shows the situation of the patient in the mouth, i.e. positively, which is obtained from an impression corresponding to the negative form. On the master model, the dental technician, with his skilful abilities, forms a model of the basic structure of the dental prosthesis to be produced in wax as well as plastic which melts at a low temperature and hardens in a polymerizing manner to obtain a positive model. This positive model is digitized, whereby known optical or mechanical methods can be used. At the same time, a gap is generated between a later dental prosthesis and tooth stump by inputting offset values to obtain the desired fit accuracy. The gap width is thereby axis-dependent, i.e. a distortion takes place, in particular in the Z direction, whereas a small gap measurement, which can go to 0, is selected in the lower peripheral area.

Independently thereof, the dimensioning of the basic structure or dental prosthesis to be produced is designed such that, with normal use, a maximum tensile stress corresponds approximately to 0.1–0.7 times the strength of the material used. To name just a few ceramics by way of example, $Al_2O_3$, zirconium oxide mixed crystals ($ZrO_2$/Y-TZP), MgO, $Y_2O_3$ or $TiO_2$ are, for example, possible materials.

When using, for example, $Al_2O_3$, care should be taken that the maximum tensile stress does not exceed 245 $N/mm^2$. However, a material deposition to a maximum tensile stress of 175 $N/mm^2$ is usually sufficient.

When producing the dental prosthesis 5 with aid of the method according to the invention, the offset value, with which the inner surface 9 of the surface model is machined to form a cement gap 7, 8 between the future dental prosthesis 5 and tooth stump 1, 2, is either set interactively by the operator or is definitely preset by programming.

The smallest gap dimensions in the area of the interface of dental prosthesis 5 and tooth stump 1, 2 and thus an especially good resistance to a later caries attack can be obtained when the gap differs from a low value on the periphery 10 of the cavity defined by the inner surface 9 of the positive model to a larger value in the tip 11 of the cavity, in particular when the gap on the periphery 10 of the cavity is less than 5 μm, preferably less than 2.8 μm, especially preferably not more than 1.5 μm.

To avoid the formation of hollow spaces between dental prosthesis 5 and tooth stump 1, 2 from which a further caries attack of the tooth stump 1, 2 and thus a destruction of the support tooth of a bridge 5 can usually be expected, it is advantageous to further conduct a test of the data of the inner surface 9 of the positive model for undercuts with reference to the data of adjacent areas of the positive model, since undercuts either result in the dental prosthesis not being able to be placed on the stump 1, 2 or a hollow space being formed.

For an especially high reliability against breakage of the dental prosthesis 5 during later use by the patient, the wall thickness of the data model is furthermore calculated by comparison of the data of the inner surface 9 of the positive model with the data of the outer surface 12 of the positive model and comparison of the value of the wall thickness with a wall thickness minimum value which can either be determined by an input of the dentist or dental technician or definitely preset by programming. When using zirconium oxide ceramic, it is expedient if the minimum value of the wall thickness is preferably about 0.1 mm to 0.3 mm.

To produce especially stable and durable bridges 5, there is preferably a calculation of the material cross-section in bridge elements in the area 13, 14 between two posts formed by the tooth stumps 1, 2 and comparison of the cross-section with a minimum value, which can be either interactively set by the operator or definitely preset by programming, and correction of the data of the outer side 12 of the positive model so that at least the minimum value is obtained, which preferably amounts to about 2 mm² to 7 mm² in yttrium oxide reinforced zirconium oxide ceramics.

What is claimed is:

1. A method for the production of a dental prosthesis to be fastened to at least one tooth stump, comprising the steps of:
   producing an impression of the region of the jaw-bone comprising the tooth stump,
   forming a master model of the region of the jaw-bone on the basis of the impression,
   forming a positive model corresponding to the dental prosthesis to be produced,
   digitizing the positive model,
   inputting offset values to form a gap between the dental prosthesis to be produced and the tooth stump,
   calculating a program on the basis of the digitized values of the positive model and the offset values for processing a material of a blank by a machine tool for producing the dental prosthesis,
   wherein the dental prosthesis to be produced is dimensioned such that under consideration of the material used for the blank, in normal use of the prosthesis, a maximum tensile stress occurs which corresponds to about 0.1–0.7 times the tensile strength of the material used.

2. A method according to claim 1 characterized in that the dental prosthesis is prepared in such a way that the maximum tensile stress in the dental prosthesis corresponds to $\leq 0.5$ times, in particular 0.2–0.5 times the tensile strength of the material used.

3. A method according to claim 1, further characterized by the following procedural steps:
   calculation of the wall thickness of the data model by comparing the data of the inner surface of the positive model with the outer surface of the positive model and comparison of the value of the wall thickness with a wall thickness minimum value, correcting the data of the outer side of the positive model that at least the wall thickness minimum value is obtained and/or a warning is issued.

4. A method according to claim 3, characterized in that the wall thickness minimum value is at least about 0.05 mm, preferably about 0.05 mm–1.0 mm, in particular 0.1 mm–0.8 mm.

5. A method according to claim 4, characterized in that the wall thickness minimum value is at least 0.3 mm.

6. A method according to claim 1, further characterized by the following step:
   calculation of the material cross-section in bridge elements in the area (13, 14) between two posts formed by the tooth stumps (1, 2), comparison of the cross-section with a minimum value, correction of the data of the outer side (12) of the positive model so that at least the minimum value is obtained and/or a warning is issued.

7. A method according to claim 6, characterized in that the minimum value of the cross-section is at least about 2 mm², preferably about 2 mm²–7 mm².

8. A method according to claim 7, characterized in that the minimum value of the cross-section is at least 7 mm².

9. A method according to claim 1, characterized in that the offset value is preset dependent on the axis.

10. A method according to claim 1, characterized in that the offset value is up to 150 μm.

11. A method according to claim 1, characterized in that the offset value on the periphery of the cavity is about $\leq 5$ μm, preferably about $\leq 2.8$ μm, in particular $\leq 1.5$ μm.

12. A method according to claim 1, further characterized by the following step:
   conduction of a plausibility test of the data with reference to the data of adjacent areas of the positive model and, optionally, issuance of a warning.

13. A method according to claim 1, further characterized by the following step:
   replacement of missing, preferably individual, data points or non-plausible data points by interpolated values with reference to the data of adjacent areas of the positive model.

14. A method according to claim 1, further characterized by the following step:
   conduction of a test of the data of the inner surface of the positive model for undercuts with reference to the data of adjacent areas and, optionally, issuance of a warning.

15. A method according to claim 1, further characterized by the following step:
   smoothing the outer and/or surface of the data model by means of a smoothing function.

16. A method according to claim 1, further characterized by the following step:
   calculation of the radii of the inner surface of the surface model, comparison of the values of the radii with a minimum radius, correction of the data of the inner surface of the positive model so that the cavity is enlarged until at least the minimum radius is obtained and/or a warning issued.

17. A method according to claim 1, further characterized by the following step:
    machining the positive model with a preset offset value to adapt it to the tool contour during the subsequent processing.

18. A method according to claim 1, further characterized by the following step:
    processing the data of the positive model with an enlargement factor to compensate shrinkage or swelling of the material for the dental prosthesis during production.

19. A method according to claim 18, characterized in that the enlargement factor is anisotropic and/or non-linear over the surface model.

20. A method according to claim 19, characterized in that the enlargement factor over the surface model is determined by a three-dimensional transfer function f(x,y,z).

21. A method according to claim 20, characterized in that the three-dimensional transfer function f(x,y,z) is determined by the three-dimensional density distribution F(x,y,z) of a ceramic blank.

22. A method according to claim 21, characterized by reading from a data carrier the transfer function f(x,y,z) or density distribution F(x,y,z) allocated to a blank to be processed.

23. A method according to claim 1, characterized in that the data carrier is a bar code label, a transponder label or a database which can be accessed via identification means applied to or supplied with the blank.

24. A method according to claim 1, further characterized by the following step:
    comparison of the radii of the outer and/or inner surfaces of the positive model with a minimum radius of at least about 0.1 mm, preferably about 0.2 mm, in particular 0.3 mm, correction of the data of the outer and/or inner surface of the positive model to the minimum radius and/or issuance of a warning.

* * * * *

UNITED STATES PATENT AND TRADEMARK OFFICE
CERTIFICATE OF CORRECTION

PATENT NO. : 6,970,760 B2
APPLICATION NO. : 10/480798
DATED : November 29, 2005
INVENTOR(S) : Dietrich Wolf et al.

It is certified that error appears in the above-identified patent and that said Letters Patent is hereby corrected as shown below:

<u>Column 8,</u>
Line 56, delete "15. A method according" to and ending "smoothing function."
and insert the following claim:
-- 15. A method according to claim 1, further characterized by the following step: smoothing the outer and/or inner surface of the data model by means of a smoothing functon. --.

Signed and Sealed this

Twenty-seventh Day of June, 2006

JON W. DUDAS
*Director of the United States Patent and Trademark Office*